United States Patent [19]

Lantzsch et al.

[11] 4,069,257

[45] Jan. 17, 1978

[54] PROCESS FOR PREPARING 2-ACETYL-3-METHYL-1,3-BUTADIENE

[75] Inventors: Reinhard Lantzsch; Dieter Arlt, both of Cologne, Germany

[73] Assignee: Bayer Aktiengesellschaft, Leverkusen, Germany

[21] Appl. No.: 631,262

[22] Filed: Nov. 12, 1975

[30] Foreign Application Priority Data

Nov. 29, 1974 Germany .............................. 2456413
Nov. 29, 1974 Germany .............................. 2456514

[51] Int. Cl.² .......................................... C07C 45/18
[52] U.S. Cl. ................................... 260/595; 260/596; 260/593 R

[58] Field of Search ................................ 260/595, 596

[56] References Cited

PUBLICATIONS

Hickenbottom, Reactions of Organic Compounds, pp. 136–142, (1957).

*Primary Examiner*—James O. Thomas, Jr.
*Assistant Examiner*—James H. Reamer
*Attorney, Agent, or Firm*—Burgess, Dinklage & Sprung

[57] ABSTRACT

2-acetyl-3-methyl-1,3-butadiene is prepared by thermally decomposing 2-methyl-3-hydroxymethyl-pent-1-en-4-one or its carboxylic acid esters.

6 Claims, No Drawings

PROCESS FOR PREPARING 2-ACETYL-3-METHYL-1,3-BUTADIENE

BACKGROUND

This invention relates to a process for the preparation of 2-acetyl-3-methyl-1,3-butadiene.

Hitherto it has only been possible to prepare this compound in accordance with a complicated multistage process (Izv. Akad. Nauk. SSSR 1962, 1267–75). The known process requires lithium acetylide and mercury oxide as reagents and only permits the preparation of small quantities. The product obtainable in this way is contaminated with trimethylfurane. The known process is unsuitable for large-scale industrial synthesis of 2-acetyl-3-methyl-1,3-butadiene ("acetylisoprene").

SUMMARY

A new process for the preparation of 2-acetyl-3-methyl-1,3-butadiene has now been found, which is characterised in that 2-methyl-3-hydroxymethyl-pent-1-en-4-one or, preferably, carboxylic acid esters of 2-methyl-3-hydroxymethyl-pent-1-en-4-one, are decomposed.

DESCRIPTION

2-Methyl-3-hydroxymethyl-pent-1-en-4-one, used as the starting point for the process according to the invention, can be prepared, for example, by reaction of mesityl oxide and formaldehyde in the presence of catalytic amounts of bicyclic amidines such as 1,5-diazabicyclo[4.3.0]non-5-ene or 1,8-diazabicyclo[5.4.0]-undec-7-ene. Such bicyclic amidines are known and can be obtained by cyclisation of the corresponding N-(aminoalkyl)-lactams in the presence of acid catalysts (British Patent specification No. 1,721,924).

To prepare 2-methyl-3-hydroxymethyl-pent-1-en-4-one, mesityl oxide is employed in equimolar amounts or in excess relative to formaldehyde; preferably, about 2–10 mols of mesityl oxide employed per mol of formaldehyde. The amount of catalyst employed in the reaction mixture is in general 0.1–10 mol percent, preferably about 0.5–2 mol percent, per mol of mesityl oxide.

The reaction is carried out at temperatures between 20° and 130° C. The reaction time is, for example, 3 hours at 30° C and a few minutes at 100° C. Advantageously, the mesityl oxide and catalyst are initially introduced and formaldehyde is metered in. The 2-methyl-3-hydroxymethyl-pent-1-en-4-one can be isolated from the reaction mixture by, for example, distillation, advantageously after neutralising the basic catalyst.

The decomposition of the 2-methyl-3-hydroxymethyl-pent-1-en-4-one consists of an elimination of water whilst the decomposition of the carboxylic acid esters consists of a pyrolytic elimination of the carboxylic acid on which the esters are used.

In principle, the elimination of water from the 2-methyl-3-hydroxymethyl-pent-1-en-4-one can be effected without the aid of catalysts. However, decomposition products are formed at the high temperatures required in that case. Hence, the elimination of water is preferably carried out in the presence of catalysts, in particular basic catalysts or, particularly preferentially, acid catalysts.

Examples of basic catalysts which can be used are: the hydroxides of the alkali metals, such as, for example, NaOH or KOH, as the solid or in aqeuous or alcoholic solution the oxides of the alkaline earth metals, for example CaO or MgO; and tertiary or heterocyclic amines, which are relatively high-boiling, such as, for example: N,N-dimethylaniline, N,N-diethylaniline, N,N-dimethyl-cyclohexylamine, 1,4-diazabicyclo-(2,2,2)-octane, 1,5-diazabicyclo-(4,3,0)-non-5-ene, 1,8-diazabicyclo-(5,4,0)-undec-7-ene, collidine and quinoline.

Examples of acid catalysts which can be used are: $KHSO_4$, $NaHSO_4$, $MgSO_4$, salts of amines, iodine, carboxylic acids, for example acetic acid, oxalic acid and formic acid, as well as anhydrides, for example phthalic anhydride. It is also possible to use $Al_2O_3$, zirconium-(IV) oxide, thorium-(IV) oxide, aluminium silicates and acid ion exchangers.

The elimination of water takes place, in the presence of basic catalysts, in general at 30 to 350° C, preferably at temperatures between 30° and 120° C, and particularly preferentially between 50° and 80° C, whilst in the presence of acid catalysts it preferably takes place between 150° and 350° C, and particularly preferentially between 200° and 300° C.

The elimination of water can be carried out under normal pressure, but is preferably carried out under reduced pressure, if appropriate whilst passing a stream of inert gas, for example a stream of nitrogen, over the mixture. The 2-acetyl-3-butadiene can be distilled off with the water formed.

Examples of carboxylic acid esters of 2-methyl-3-hydroxymethyl-pent-1-en-4-one which are suitable are esters of lower saturated aliphatic carboxylic acids or benzoic acid. Preferred aliphatic carboxylic acids are those with 1 – 5 carbon atoms in the molecule. Particularly preferred carboxylic acids are formic acid, acetic acid, propionic acid or benzoic acid.

2-Methyl-3-hydroxymethyl-pent-1-en-4-one is converted, according to methods which are in themselves known for esterification reactions, for example by reaction with the particular carboxylic acids, carboxylic acid chlorides, carboxylic acid anhydrides or carboxylic acid esters (transesterification), into the carboxylic acid esters used as the starting material for the process according to the invention.

The pyrolysis, according to the invention, of the carboxylic acid esters is carried out by heating the carboxylic acid esters to temperatures of about 300° – 600° C, preferably to about 350° – 500° C.

It has proved advantageous also to carry out the pyrolysis according to the invention in an inert gas atmosphere, for example nitrogen. To avoid the polymerisation of the 2-acetyl-3-methyl-1,3-butadiene formed, the process according to the invention is suitably carried out in the presence of one of the customary polymerisation inhibitors, for example in the presence of hydroquinone or a phenol with branched alkyl substituents in the ortho-position.

Furthermore it has proved advantageous to cool the product, obtainable according to the process of the invention, to temperatures which are as low as possible, suitably below 0° C.

To carry out the ester pyrolysis according to the invention in practice, it is possible, for example, to introduce the liquid starting material (carboxylic acid ester) dropwise into a glass tube or quartz tube filled with Raschig rings, which is heated to the temperature used for the process according to the invention. The reaction product collected in a cooled receiver can be subjected to a fractional vacuum distillation in order to isolate the 2-acetyl-3-methyl-1,3-butadiene.

The decomposition of 2-methyl-3-hydroxymethyl-pent-1-en-4-one according to the invention, but especially the pyrolysis of its carboxylic acid esters is distinguished by the fact that 2-acetyl-3-methyl-1,3-butadiene is obtained in high purity and very good yields. The yield is practically quantitative, relative to the carboxylic acid ester employed as the starting material. Because of its high purity, the product obtained can be employed directly in polymerisation reactions.

2-Acetyl-3-methyl-1,3-butadiene is an isoprene derivative and can be employed in a manner which is in itself known, for example in cationic or radical polymerisation reactions. Polymers for which this compound is used as a monomeric component, such as, for example, rubbers or thermoplastics, permit a controlled modification because of the reactivity of the keto groups, for example a crosslinking reaction with diamines.

Furthermore, the compound, being a diene, is a valuable intermediate product for Diels-Alder reactions, for example for the manufacture of new plant protection preparations.

E.g. the Diels-Alder addition product 5,8-dihydro-6-acetyl-7-methyl-1,4-dihydroxy-naphthalene (m.p. 226° – 228° C with decomposition) obtained by the addition of 2-acetyl-3-methyl-1,3-butadiene to p-benzochinone shows good effectiveness against fungi tiletia caries (bunt of wheat) and venturia inaequalis (apples scab).

In the spore germination test with venturia inaequalis a complete inhibition of spore germination was achieved at an active compound concentration of 0.0005%.

In a test where the compound is used as a dressing material on wheat grains a complete inhibition of spore germination of tiletia caries is achieved at an active compound concentration of 2%.

EXAMPLE 1

69.6 g (0.3 mol) of 2-methyl-3-benzoyloxymethyl-pent-1-en-4-one were dripped through a glass tube heated to 450° C, which was filled with Raschig rings. At the same time a slight stream of nitrogen was passed through the tube. Hydroquinone was present as the polymerisation inhibitor in the well-cooled receiver. The product was dried with a zeolite. The benzoic acid which separated out, and the zeolite, were filtered off, and the crude product was distilled in a high vacuum. 20 g (61%) of pure 2-acetyl-3-methyl-1,3-butadiene were obtained.

Boiling point: B.p. = 30°–33° C/0.6 mm Hg

Elementary analysis
$C_7H_{10}O$ (M = 110.15)
Calculated: C 76.2  H 9.1
Found    : C 76.1  H 9.3
Nuclear resonance spectrum (in $CDCl_3$):

| | |
|---|---|
| Triplet at δ=1.9 ppm | 3 protons |
| Singlet at δ=2.3 ppm | 3 protons |
| Singlet at δ=5.05 ppm | 4 protons |
| Doublet at δ=5.7 ppm | |

2-Methyl-3-benzoyloxymethyl-pent-1-en-4-one, used as the starting compound, was prepared as follows:

64 g of 2-methyl-3-hydroxymethyl-pent-1-en-4-one were dissolved in 200 ml of pyridine and 85 g of benzoyl chloride were added dropwise whilst cooling with ice. After warming to 100° C for 15 minutes, the reaction mixture is poured onto ice, acidified with concentrated hydrochloric acid and extracted with ether. The ether phase was washed with sodium bicarbonate solution and then with water. After drying with sodium sulphate, the ether was stripped off on a rotary evaporator. Fractional distillation in a high vacuum gave 89 g of 2-methyl-3-benzoyloxy-methyl-pent-1-en-4-one of boiling point 122° – 126° C/0.05 mm Hg.

2-Methyl-3-hydroxymethyl-pent-1-en-4-one was obtained as follows:

30 g (1 mol) of paraformaldehyde were added to a mixture of 490 g (5 mols) of mesityl oxide and 15.2 g (0.1 mol) of 1,8-diazabicyclo[5.4.0]undec-7-ene over the course of 2 – 3 hours at 30° C. After completion of the addition of formaldehyde, the reaction mixture was stirred for about a further hour, then cooled to 0° C and neutralised with dilute hydrochloric acid. The organic phase was separated off and the aqueous phase was repeatedly extracted with methylene chloride. The combined organic phases were dried with zeolite, filtered off and then freed from methylene chloride. The residue (506 g) was fractionally distilled in a high vacuum at about 0.1 – 1 mm Hg. Thereby, 431 g of mesityl oxide were recovered. As a further fraction, 47 g of crude product of boiling point 45° – 85° C/1 mm Hg were obtained. A further fractional distillation of this crude product gave 35.5 g of 2-methyl-3-hydroxymethyl-pent-1-en-4-one of boiling point 50° – 52° C/0.2 mm Hg (yield: 78%, relative to mesityl oxide converted), in the form of a colourless liquid.

EXAMPLE 2

85 g (0.5 mol) of 2-methyl-3-acetoxymethyl-pent-1-en-4-one were dripped over the course of half an hour through a tube which was heated to 400° C and filled with Raschig rings. Hydroquinone was present as a polymerisation inhibitor in the receiver, which was cooled with solid carbon dioxide/acetone.

84 g (99%) of 2-acetyl-3-methyl-1,3-butadiene, dissolved in acetic acid, were obtained. According to analysis by gas chromatography the solution contained 64.1% (corresponding to a yield of > 99%) of the product. To isolate the 2-acetyl-3-methyl-1,3-butadiene, the reaction mixture was subjected to a fractional distillation as in Example 1.

2-Methyl-3-acetoxy-methyl-pent-1-en-4-one, used as the starting compound, was prepared as follows:

256 g (2 mols) of 2-methyl-3-hydroxymethyl-pent-1-en-4-one were boiled for three hours under reflux with 1,000 ml of acetic anhydride. The acetic acid produced, and the excess acetic anhydride, were than distilled off in a waterpump vacuum. The residue was distilled in a high vacuum. 249 g of 2-methyl-3-acetoxymethyl-pent-1-en-4-one of boiling point 52° – 55° C/0.05 mm Hg were obtained.

EXAMPLE 3

64 g (0.5 mol) of 2-methyl-3-hydroxymethyl-pent-1-en-4-one are dripped over the course of half an hour onto 300 mg of pulverulent potassium hydroxide contained in a distillation apparatus. The bath temperature is 60° C and the pressure about 0.5 mm Hg. A polymerisation inhibitor (2,6-bis-tert.-butyl-phenol) is present in the flask and in the receiver. The 2-acetyl-3-methyl-1,3-butadiene formed distils off together with water and is collected in the well-cooled receiver. 51 g of distillate, containing 9 g of water, are obtained. Composition of the dried distillate: 90% of 2-acetyl-3-methyl-1,3-butadiene and 10% of mesityl oxide.

EXAMPLE 4

64 g (0.5 mol) of 2-methyl-3-hydroxymethyl-pent-1-en-4-one are dripped over the course of half an hour onto 3 ml of 1,8-diazabicyclo[5.4.0]undec-7-ene contained in a distillation apparatus. The bath temperature is 70° C and the pressure about 0.5 mm Hg. A polymerisation inhibitor is present in the flask and in the receiver. The 2-acetyl-3-methyl-1,3-butadiene formed distils off with the water and is collected in the well-cooled receiver. 52 g of distillate containing 9 g of water are obtained. Composition of the dried distillate: 90% of 2-acetyl-3-methyl-butadiene and 8.5% of mesityl oxide.

EXAMPLE 5

32 g (0.25 mol) of 2-methyl-3-hydroxymethyl-pent-1-en-4-one are dripped over the course of half an hour onto 34 g (0.25 mol) of potassium bisulphate which is contained in a distillation apparatus. The bath temperature is 200° C and the pressure is about 15 - 20 mm Hg. A polymerisation inhibitor is present in the flask and in the receiver. According to analysis by gas chromatography, the distillate contains 30% of 2-acetyl-3-methyl-butadiene = 58.9% relative to 2-methyl-3-hydroxymethyl-pent-1-en-4-one converted, 55% of starting compound and 6.7% of dimeric 2-acetyl-3-methyl-butadiene. The 2-acetyl-3-methyl-butadiene can be separated from the 2-methyl-3-hydroxymethyl-pent-1-en-4-one by distillation (boiling point: 30° - 33° C/0.6 mm Hg).

EXAMPLE 6

32 g (0.25 mol) of 2-methyl-3-hydroxymethyl-pent-1-en-4-one are dripped over the course of 40 minutes onto 67.5 g of anhydrous oxalic acid contained in a distillation apparatus. A slow stream of nitrogen is passed through the apparatus. The bath temperature is 180° C and the pressure about 760 mm Hg. A polymerisation inhibitor is present in the flask and in the well-cooled receiver. 26 g of distillate are obtained; this contains 50% of 2-acetyl-3-methyl-1,3-butadiene.

EXAMPLE 7

50 to 100 mg of iodine are added to 64 g (0.5 mol) of 2-methyl-3-hydroxymethyl-pent-1-en-4-one and the mixture is distilled at 80° C external temperature, in a high vacuum (about 0.2 - 1 mm Hg.), using a Vigreux column, in such a way that the top temperature does not rise above 40° C. A polymerisation inhibitor is contained in the well-cooled receiver. The 2-acetyl-3-methyl-1,3-butadiene formed distils off with the water. After separating off the water, the distillate contains 98% of 2-acetyl-3-methyl-1,3-butadiene and only traces of mesityl oxide.

What is claimed is:

1. A process for preparing 2-acetyl-3-methyl-1,3-butadiene which comprises:
   A. contacting mesityl oxide with formaldehyde in the presence of 0.1 to 10 mol percent of a bicyclic amidine per mol of mesityl oxide whereby to obtain 2-methyl-3-hydroxymethyl-pent-1-en-4-one; and B. heating said 2-methyl-3-hydroxymethyl-pent-1-en-4-one at 300° to 600° C until it decomposes.

2. A process for preparing 2-acetyl-3-methyl-1,3-butadiene which comprises:
   A. forming 2-methyl-3-hydroxymethyl-pent-1-en-4-one by contacting mesityl oxide with formaldehyde in the presence of a catalytic amount of a bicyclic amidine;
   B. contacting said 2-methyl-3-hydroxymethyl-pent-1-en-4-one with a carboxylic acid, carboxylic acid chloride, carboxylic acid anhydride or carboxylic acid ester whereby to form the carboxylic acid ester of 2-methyl-3-hydroxymethyl-pent-1-en-4-one; and
   C. heating said carboxylic acid ester of 2-methyl-3-hydroxymethyl-pent-1-en-4-one until it decomposes.

3. A process according to claim 3 wherein said 2-methyl-3-hydroxymethyl-pent-1-en-4one is contacted with formic acid ester, an acetic acid ester, a propionic acid ester or a benzoic acid ester to form the corresponding carboxylic acid ester.

4. A process for preparing 2-acetyl-3-methyl-1,3-butadiene which comprises:
   A. contacting mesityl oxide with formaldehyde in the presence of 0.1 to 10 mol percent of a bicyclic amidine per mol of mesityl oxide whereby to obtain 2-methyl-3-hydroxymethyl-pent-1-en-4-one; and
   B. heating said 2-methyl-3-hydroxymethyl-pent-1-en-4-one in the presence of an acid or basic catalyst until it decomposes.

5. Process of claim 4 wherein the heating of said 2-methyl-3-hydroxymethyl-pent-1-en-4-one is effected at temperatures of from 30° to 350° C.

6. Process of claim 2 carried out at about 300° to 600° C.

* * * * *

UNITED STATES PATENT AND TRADEMARK OFFICE
CERTIFICATE OF CORRECTION

PATENT NO. : 4,069,257

DATED : January 17, 1978

INVENTOR(S) : Reinhard Lantzsch et al

It is certified that error appears in the above—identified patent and that said Letters Patent are hereby corrected as shown below:

[56] References Cited, Title Page, add the following:

U.S. Patent Documents

| | | | |
|---|---|---|---|
| 2,139,360 | 12/38 | Fairband et al | 260/596 |
| 2,256,149 | 9/41 | Long | 260/595 |
| 2,380,828 | 7/45 | Dreisbach et al | 260/596 |
| 2,794,837 | 6/57 | Grimme et al | 260/596 |
| 3,259,658 | 7/66 | Mercier et al | 260/596 |

Column 1, line 56, "used" should read -- based --.

Column 1, line 68, insert -- ; -- after "solution".

Column 2, line 26, delete "butadiene" after "3-", and insert -- methyl-1,3-butadiene --.

Column 4, line 49, "than" should read -- then --.

Column 6, line 12, "B." should start new line.

Column 6, line 31, "-4one" should read -- -4-one --.

Signed and Sealed this

Twentieth Day of June 1978

[SEAL]

Attest:

RUTH C. MASON
*Attesting Officer*

DONALD W. BANNER
*Commissioner of Patents and Trademarks*